United States Patent
Lin et al.

(10) Patent No.: US 6,524,622 B1
(45) Date of Patent: Feb. 25, 2003

(54) METHOD OF CONTROLLING THE WORKING TIME OF A GYPSUM COMPOSITION IN THE BONE TREATMENT

(75) Inventors: Shengfu Lin, Taipei (TW); Chih-I Lin, Chino Hills, CA (US); Horng Wei Pan, Keelung (TW); Shao-Wen Wu, Taipei (TW); Wen-Ching Say, Taipei (TW)

(73) Assignee: Central Medical Technologies Inc., Taipei (TW)

( * ) Notice: Subject to any disclaimer, the term of this patent is extended or adjusted under 35 U.S.C. 154(b) by 0 days.

(21) Appl. No.: 10/196,235

(22) Filed: Jul. 17, 2002

(30) Foreign Application Priority Data

Dec. 21, 2001 (TW) .......................................... 90131954 A

(51) Int. Cl.$^7$ ........................ A61K 35/14; A61K 35/16; A61K 33/06; A61F 2/00
(52) U.S. Cl. ........................ 424/529; 424/423; 424/530; 424/531; 424/696
(58) Field of Search ................................. 424/423, 529, 424/530, 531, 696

(56) References Cited

U.S. PATENT DOCUMENTS 6,251,139 B1 * 6/2001 Lin et al. .................. 623/17.11

* cited by examiner

*Primary Examiner*—Raymond Henley, III
(74) *Attorney, Agent, or Firm*—Bacon & Thomas, PLLC

(57) ABSTRACT

A method is designed to control the working time, setting time and the semi-solidification time of a gypsum composition in a bone restoration operation. The method involves a preparation of the gypsum composition by mixing an orthopedic gypsum and an aqueous solution in a weight ratio to form a semisolid substance which is to be injected into a patient under treatment. The aqueous solution contains serum, blood plasma, or whole blood, which is preferably taken from the patient under treatment.

10 Claims, No Drawings

METHOD OF CONTROLLING THE WORKING TIME OF A GYPSUM COMPOSITION IN THE BONE TREATMENT

FIELD OF THE INVENTION

The present invention relates generally to the use of a gypsum composition in treating a deformed or injured bone, and more particularly to a method of controlling the working time of the gypsum composition in the course of treating the deformed or injured bone.

BACKGROUND OF THE INVENTION

The gypsum has been used as a bone substituent in the conventional surgical treatment of the bone deformities. The new surgical operation makes use of the gypsum as a bone substituent by injection. The technique disclosed in U.S. Pat. No. 6,251,139 is the case in point. The conventional gypsum composition is rather limited in its semi-solidification time and its working time. The phrase "the working time" refers to the duration between the time when the orthopedic gypsum is mixed with an aqueous solution to form a gypsum composition and the time at which the gypsum composition can hardly be ejected from a syringe. The phrase "the semi-solidification time" refers to the period of time starting from the time at which the orthopedic gypsum is mixed with an aqueous solution to the time at which the gypsum composition does not disperse in water or an aqueous solution such as physiological salt water, into which the gypsum composition is introduced. For example, the semi-solidification time of the conventional gypsum composition ranges from 2.5 minutes to 3.0 minutes, whereas the working time of the conventional gypsum composition ranges from 3.5 minutes to 4.0 minutes. In other words, the conventional gypsum composition will disperse in body liquid if it is injected into human body within 2.5 minutes starting from the time at which the orthopedic gypsum is mixed with an aqueous solution. It is likely that the conventional gypsum composition can not be injected into the body of a patient if the attending surgeon fails to administer the injection in 4.0 minutes starting from the time at which the orthopedic gypsum is mixed with an aqueous solution. Accordingly, only about one and a half minutes for the attending surgeon to complete the injection of the conventional gypsum composition into the body of a patient. It is conceivable that the attending surgeon is under pressure to rush the restorative operation at the expense of the well-being of the patient. It is therefore crucial to control the working time and the semi-solidification time of a gypsum composition.

SUMMARY OF THE INVENTION

The primary objective of the present invention is to provide a gypsum composition containing serum, blood plasma, or whole blood, so as to control the working time, setting time and the semi-solidification time of the gypsum composition. The gypsum composition further contains bone morphogenetic proteins which promote the growth of bone cells.

The gypsum composition of the present invention is prepared by mixing an orthopedic gypsum and an aqueous solution. The mixture is uniformly agitated to form a semi-solid substance. Specifically, the mixture is formed by the orthopedic gypsum and the aqueous solution in a weight ratio ranging between 5:1 and 2:1. The gypsum composition of the present invention is characterized by the aqueous solution which contains serum, blood plasma, or whole blood in a volume percentage ranging between 2% and 40%.

The agitation of the mixture of the present invention is brought about by an agitation bar, magnetic agitator, or ultrasonic vibrator.

The weight ratio of the orthopedic gypsum and the aqueous solution in the present invention ranges preferably between 4:1 and 3:1. The volume percentage of the serum, blood plasma, or whole blood in the present invention ranges preferably between 4% and 35%. The serum, blood plasma, or whole blood is preferably taken from a patient under treatment.

The aqueous solution of the present invention further contains less than 10% by weight of a setting promoter, such as polyol, polysaccharide, polyvinyl alcohol, etc.

The gypsum composition of the present invention may further contain a specific substance, which is intended to attain a specific objective, such as promotion of bone cell growth or prevention of inflammation. If the specific substance is solid, it must be thoroughly dissolved in the aqueous solution. If the specific substance is liquid, it must be thoroughly mixed with the aqueous solution.

The orthopedic gypsum used in the present invention preferably is calcium sulfate half-hydrate ($CaSO_4 \cdot 0.5H_2O$), abbreviated as half-hydrate gypsum.

The features and the advantages of the present invention will be more readily understood upon a thoughtful deliberation of the following descriptions of the preferred embodiments of the present invention. These preferred embodiments are to be regarded in all respects as being merely illustrative and nonrestrictive.

DETAILED DESCRIPTION OF THE PREFERRED EMBODIMENTS

Examples 1–6

In these examples, 12 g of half-hydrate gypsum was used. The half-hydrate gypsum was mixed with water for 30 seconds, then blood plasma was added, and the resulting mixture was agitated for another 2 minutes. The results of the embodiments are shown in the following Table 1.

TABLE 1

| | Aqueous solution | | Working | Setting | Semi- |
| --- | --- | --- | --- | --- | --- |
| Ex. | Water (ml) | Blood plasma (ml) | time (min) | time (min) | solidification time (min) |
| 1 | 2.4 | 0.1 | <10 | 20–22 | 4 |
| 2 | 2.3 | 0.2 | <10 | 20–22 | 4.5 |
| 3 | 2.1 | 0.4 | <12 | 22–25 | 5.0 |
| 4 | 2.0 | 0.5 | <11 | 22–25 | 5.0 |
| 5 | 1.9 | 0.6 | <14 | 28–30 | 5.5 |
| 6 | 1.7 | 0.8 | <15 | 30–32 | 6.0 |

Examples 7–8

These examples are basically similar to Example 4, with the differences being that 0.5 ml of whole blood was used in the Example 7 in place of the plasma in Example 4, and that 0.5 ml of serum was used in Example 8 in place of the plasma in Example 4. The results are shown in the following Table 2.

TABLE 2

| Ex. | Working time | Setting time | Semi-solidification time |
| --- | --- | --- | --- |
| 7 | <14 minutes | 32–35 minutes | 6 minutes |
| 8 | <25 minutes | 110–120 minutes | 10 minutes |

Examples 9–12

In these examples, 10 grams of half-hydrate gypsum was mixed with an aqueous solution prepared with the composition listed in Table 3. The agitation time was 2.5 minutes.

The results are shown in the following Table 3.

TABLE 3

| Ex. | Aqueous solution | | | | Working time (min) | Setting time (min) | Semi-solidification time (min) |
| --- | --- | --- | --- | --- | --- | --- | --- |
| | Water (ml) | Blood plasma (ml) | Methyl cellulose (ml) | glycerol (ml) | | | |
| 9 | 1.8 | 0.2 | 0.5 | 0.2 | 7 | 25–28 | 4 |
| 10 | 1.6 | 0.4 | 0.5 | 0.2 | 16 | 25–28 | 5 |
| 11 | 1.4 | 0.6 | 0.5 | 0.2 | 17 | 30–32 | 5 |
| 12 | 1.0 | 1.0 | 0.5 | 0.2 | 25 | 60–65 | 8 |

What is claimed is:

1. A gypsum composition for use in bone treatment, said composition containing an orthopedic gypsum and an aqueous solution in a weight ratio ranging between 5:1 and 2:1; wherein said aqueous solution contains serum, blood plasma, or whole blood in a volume percentage ranging between 2% and 40%.

2. The composition as defined in claim 1, wherein said weight ratio ranges between 4:1 and 3:1.

3. The composition as defined in claim 1, wherein said volume percentage ranges between 4% and 35%.

4. The composition as defined in claim 2, wherein said volume percentage ranges between 4% and 35%.

5. The composition as defined in claim 1, wherein the serum, blood plasma, or whole blood is taken from a patient under treatment.

6. The composition as defined in claim 4, wherein the serum, plasma, or whole blood is taken from a patient under treatment.

7. The composition as defined in claim 1, wherein said aqueous solution further contains less than 10% by weight of a setting promoter selected from the group consisting of polyol, polysaccharide, and polyvinyl alcohol.

8. The composition as defined in claim 4, wherein said aqueous solution further contains less than 10% by weight of a setting promoter selected from the group consisting of polyol, polysaccharide, and polyvinyl alcohol.

9. The composition as defined in claim 6, wherein said aqueous solution further contains less than 10% by weight of a setting promoter selected from the group consisting of polyol, polysaccharide, and polyvinyl alcohol.

10. The composition as defined in claim 1, wherein said orthopedic gypsum is calcium sulfate half-hydrate ($CaSO_4 \cdot 0.5H_2O$).

* * * * *